United States Patent [19]
Hu et al.

[11] Patent Number: 5,469,486
[45] Date of Patent: * Nov. 21, 1995

[54] PROJECTION DOMAIN RECONSTRUCTION METHOD FOR HELICAL SCANNING COMPUTED TOMOGRAPHY APPARATUS WITH MULTI-COLUMN DETECTOR ARRAY EMPLOYING OVERLAPPING BEAMS

[75] Inventors: Hui Hu, Waukesha, Wis.; Norbert J. Pelc, Los Altos, Calif.; Armin H. Pfoh, New Berlin, Wis.

[73] Assignee: General Electric Company, Waukesha, Wis.

[*] Notice: The portion of the term of this patent subsequent to Jul. 4, 2012, has been disclaimed.

[21] Appl. No.: 151,456

[22] Filed: Nov. 8, 1993

Related U.S. Application Data

[63] Continuation-in-part of Ser. No. 8,928, Jan. 26, 1993, Pat. No. 5,430,783, which is a continuation-in-part of Ser. No. 945,758, Sep. 16, 1992, Pat. No. 5,377,250, which is a continuation-in-part of Ser. No. 926,987, Aug. 7, 1992, Pat. No. 5,291,402.

[51] Int. Cl.⁶ .......................... A61B 6/03; G01N 23/083
[52] U.S. Cl. .................... 378/4; 378/901; 364/413.17
[58] Field of Search .................. 378/4, 14, 15, 378/901; 364/413.15, 413.16, 413.17

[56] References Cited

U.S. PATENT DOCUMENTS

| | | | |
|---|---|---|---|
| 4,086,492 | 4/1978 | Lodge et al. | 378/98.2 |
| 4,293,912 | 10/1981 | Walters | 364/413.12 |
| 4,352,021 | 9/1982 | Boyd et al. | 378/12 |
| 4,442,489 | 4/1984 | Wagner | 364/413.15 |
| 4,888,693 | 12/1989 | Tam | 364/413.16 |
| 4,965,726 | 10/1990 | Heuscher et al. | 364/413.19 |
| 5,216,601 | 6/1993 | Crawford et al. | 364/413.16 |
| 5,228,069 | 7/1993 | Arenson et al. | 378/19 |
| 5,241,576 | 8/1993 | Lonn | 378/19 |
| 5,253,171 | 10/1993 | Hsiao et al. | 364/413.19 |
| 5,291,402 | 3/1994 | Pfoh | 364/413.14 |
| 5,377,250 | 12/1994 | Hu | 378/15 |
| 5,396,528 | 3/1995 | Hu et al. | 378/14 |
| 5,400,377 | 3/1995 | Hu et al. | 378/8 |

FOREIGN PATENT DOCUMENTS 2088670 6/1982 United Kingdom.

OTHER PUBLICATIONS

*Practical cone-beam algorithm*, L. A. Feldkamp et al., J. Opt. Soc. Am. A/vol. 1, No. 6, Jun. 1984, Optical Society of America pp. 612–619.

*The Theory of Three-Dimensional Image Reconstruction for PET*, J. G. Rogers, et al., IEEE Transactions on Medical Imaging, vol. MI–6, No. 3, Sep. 1987. pp. 239–243.

*Iterative Three-dimensional Reconstruction From Twin-Cone Beam Projections*, IEEE Transactions on Nuclear Science, vol. NS–25, No. 5, Oct. 1978. pp. 1135–1143.

Primary Examiner—David P. Porta
Assistant Examiner—David Vernon Bruce
Attorney, Agent, or Firm—Quarles & Brady

[57] ABSTRACT

An x-ray computed tomography system for helically scanning a patient translates the patient as projections of the patient at various beam angles are obtained. The projection data are weighted prior to reconstruction to account for multiply measured projection data and the deviation of the cone beam from a parallel beam approximation.

8 Claims, 5 Drawing Sheets

PROJECTION DOMAIN RECONSTRUCTION METHOD FOR HELICAL SCANNING COMPUTED TOMOGRAPHY APPARATUS WITH MULTI-COLUMN DETECTOR ARRAY EMPLOYING OVERLAPPING BEAMS

This application is a continuation-in-part of U.S. application No. 08/008,928 filed Jan. 26, 1993 now U.S. Pat. No. 5,430,783 and entitled "Reconstruction Method For Helical Scanning Computed Tomography Apparatus With Multi-Row Detector Array Employing Overlapping Beams" which is a continuation-in-part of U.S. application No. 07/945,758 filed Sep. 16, 1992 now U.S. Pat. No. 5,377,250 and entitled "Reconstruction Method For Helical Scanning Computed Tomography Apparatus With Multi-Row Detector Array" which is a continuation-in-part of U.S. application No. 07/926,987 filed Aug. 7, 1992 now U.S. Pat. No. 5,291,402 and entitled "Helical Scanning Computed Tomography Apparatus With Multi-Row Detector Array".

BACKGROUND OF THE INVENTION

This invention relates to computed tomography ("CT") systems where the patient is moved continuously during the scanning and more specifically to a CT apparatus employing multiple columns of detector elements displaced along the axis of patient movement.

Helical CT Scanning

Fan beam CT imaging systems are well known for producing detailed tomographic views of a patient or other imaged object. Generally a number of x-ray projections are acquired at a range of angles about the patient and within a slice plane to form a projection set. The projection set is reconstructed to form a slice image, being a cross-section along the imaging plane.

A typical CT study entails the acquisition of a series of adjacent slice images between which the patient is repositioned. A reduction in patient repositioning time may be accomplished by translating the patient along the z-axis synchronously with the rotation of the gantry. The combination of constant patient translation and acquisition of CT projection data, has been termed "helical scanning" and refers to the apparent helical path of the center of the x-ray beam with respect to the imaged object. Unfortunately, helical scanning may introduce certain errors in the reconstructed slice images.

The mathematics of tomographic reconstruction assumes that the tomographic projection set is acquired along a constant z-axis slice plane. The helical scan path clearly deviates from this condition and this deviation results in image artifacts in the reconstructed slice image. The severity of the image artifacts depends generally on the "helix offset" in the projection data, measured as the difference between the z-axis location of the scanned data and the z-axis location of the desired slice plane. Errors resulting from helical scanning will be referred to collectively as "skew" artifacts.

Skew artifacts may be reduced by interpolating and/or extrapolating between the data of projection sets acquired at certain different beam angles and hence at different translational positions with respect to the patient.

A drawback to interpolation and extrapolation in correcting helically scanned data is that these processes reduce the resolution of the acquired projection data along the z-axis by increasing the effective beam profile along the z-axis. The spatial resolution of a CT system is a measure of the smallest object that may be resolved by the CT system. All other conditions being equal, higher resolution (the ability to image smaller objects) is preferred.

Co-pending U.S. application No. 07/926,987 filed Aug. 7, 1992 now issued as U.S. Pat. No. 5,291,402 and entitled: HELICAL SCANNING COMPUTED TOMOGRAPHY APPARATUS WITH MULTI-COLUMN DETECTOR ARRAY describes an apparatus for improving the effective spatial resolution of a helical CT system by combining the signals from columns of a sub-divided detector having multiple narrow columns of detector elements. Co-pending U.S. application No. 07/945,758 filed Sep. 16, 1992 now issued as U.S. Pat. No. 5,377,250 and entitled: RECONSTRUCTION METHOD FOR HELICAL SCANNING COMPUTED TOMOGRAPHY APPARATUS WITH MULTI-COLUMN DETECTOR ARRAY teaches an improved backprojection method that more accurately accommodates the effect of the divergence of a fan beam along the translational axis when used with a multi-column detector. Co-pending U.S. application No. 08/008,928 filed Jan. 26, 1992 and entitled: RECONSTRUCTION METHOD FOR HELICAL SCANNING COMPUTED TOMOGRAPHY APPARATUS WITH MULTI-COLUMN DETECTOR ARRAY EMPLOYING OVERLAPPING BEAMS teaches a way to accommodate the multiply measured data, necessarily obtained in a helical scan with a multi-column detector, by combining and weighting the data during the backprojection of the raw data to an image. The parent application also employs a "cone beam" reconstruction method to account for the extra width of the fan beam which more closely approximates a cone.

SUMMARY OF THE INVENTION

The present invention provides a method of reconstructing the data obtained with a multi-column detector that can make use of standard fan beam reconstruction techniques by weighting the projection data prior to its reconstruction—rather than during the reconstruction as done in the parent case. The result is a reconstruction process that is simpler and typically faster.

Specifically, the invention employs an x-ray source directing a beam of x-rays along a beam axis with rotation of the beam axis throughout a plurality of beam angles about a translation axis, the beam including a plurality of rays along paths diverging across a translation axis and about a central cone axis at ray angles. The beam is received, after it passes through an imaged object, by an array of detector elements. Each element produces an intensity signal dependant on the attenuation of the ray of x-rays associated with that element.

During the rotation of the beam axis, the imaged object is moved along the translation axis with respect to the x-ray source throughout a plurality of translation positions so that some voxels of the imaged object are illuminated by a first ray at a first beam angle and a second ray at a second beam angle, the first ray and the second ray being associated with beam angles differing by an integer multiple of $2\pi$ radians. The intensity signals associated with the first and second ray are weighted, prior to reconstruction of a tomographic image, to produce weighted intensity signals which are reconstructed into a tomographic image that may be displayed.

It is one object of the invention to make use of the additional projection information present in a cone beam scan (as is required to ensure that the imaged object is at all points illuminated by at least 2π of beam angle) to decrease the effect of the abrupt change in ray angle at the first and last projections of the projection set which may produce image artifacts.

DETAILED DESCRIPTION OF THE PREFERRED EMBODIMENT

Figure 1:
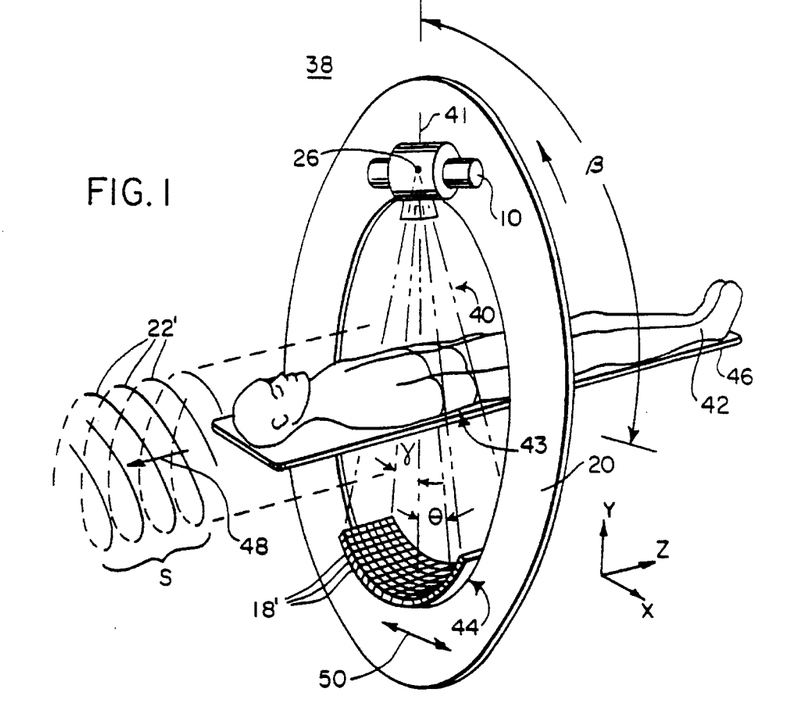
FIG. 1 is a pictorial representation of the CT apparatus of the present invention including a detector array having rows and columns of detector elements and a fan beam.

Referring to FIG. 1, a CT scanner for use with the present invention includes a gantry 20 supporting an x-ray source 10 oriented to project a fan beam 40 of x-rays along a beam axis 41 through a patient 42 to a supported and opposed detector array 44. The gantry 20 rotates to swing the beam axis within a gantry plane 38 defining the x–y plane of a Cartesian coordinate system. Rotation of the gantry 20 is measured by beam angle β from an arbitrary reference position within the gantry plane 38.

The patient 42 rests on a table 46 that may be moved along a translation axis 48 aligned with the z-axis of the Cartesian coordinate system. The table 46 crosses the gantry plane 38 and is radiotranslucent so as not to interfere with the imaging process.

The x-rays of the fan beam 40 diverge from the beam axis 41 and the gantry plane 38, across the translation axis 48 at a ray angle θ, and also diverge from the beam axis 41 within the gantry plane 38 across a transverse axis 50 generally orthogonal to both the beam axis 41 and the translation axis 48 at a fan beam angle γ.

After passing through the patient 42, the x-rays of the fan beam 40 are received by the detector array 44, which unlike the detector of a conventional fan beam CT has multiple columns of detector elements 18'. The detector elements 18' are arranged in columns extending along the transverse axis 50 and rows extending along the translation axis 48. The surface of the detector array 44 may be planar or may describe a section of the surface of a sphere or cylinder having a center at the focal spot 26.

The detector elements 18' each receive x-rays and provide intensity measurements along separate rays of the fan beam 40. The intensity measurements together describe the attenuation of the fan beam 40 by a volume 43 of the patient 42 hence the average density of that volume 43 of the patient 42.

In the preferred embodiment, this volume is substantially equal to the slice volume measured by a conventional fan beam CT system, and the width of the detector array 44, as measured along its rows, is approximately equal to the width of a similar detector for a conventional stop and shoot fan beam system. Accordingly, the rows of detector elements 18' simply subdivide a conventional fan beam detector array along the z-axis.

Figure 2:
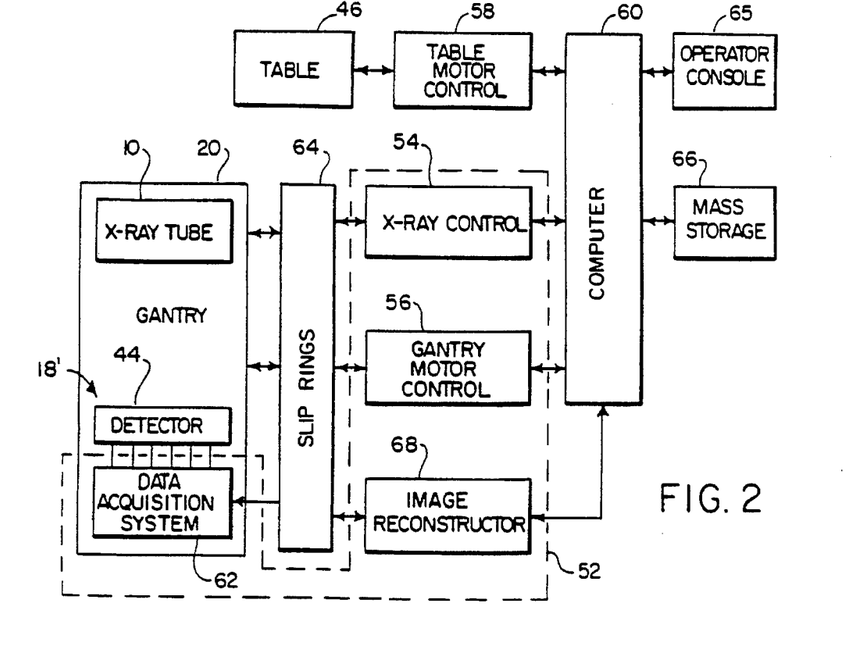
FIG. 2 is a block diagram of a CT control system that may be used with the CT apparatus of FIG. 1 and that is useful for practicing the present invention.

Referring now to FIG. 2, the control system of a CT imaging system of FIG. 1, has gantry associated control modules 52 which include an x-ray control 54, a gantry motor control 56, a data acquisition system 62 and an image reconstructor 68. The x-ray control 54 provides power and timing signals to the x-ray source 10 to turn it on and off as required under the control of a computer 60. The gantry motor control 56 controls the rotational speed and position of the gantry 20 and provides information to the computer 60 regarding gantry position. The data acquisition system 62 samples and digitizes intensity signals from the detector elements 18' of detector array 44, and the image reconstructor 68 receives the sampled and digitized intensity signals from the data acquisition system 62, each identified as to column and row of the detector element of the detector array 44, and combines the intensity signals from the detector elements 18' according to the present invention, and performs high speed image reconstruction according to methods known in the art.

Each of the above modules is connected to its associated elements on the gantry 20 via slip rings 64 and serves to interface computer 60 to various gantry functions. The slip rings 64 permit the gantry 20 to rotate continuously through angles greater than 360° to acquire projection data.

The speed and position of table 46 along the translation axis 48 is communicated to and controlled by computer 60 by means of table motor control 58. The computer 60 receives commands and scanning parameters via operator console 65 which is generally a CRT display and keyboard which allows an operator to enter parameters for the scan and to display the reconstructed image and other information from the computer 60. A mass storage device 66 provides a means for storing operating programs for the CT imaging system, as well as image data for future reference by the operator. Both the computer 60 and the image reconstructor have associated electronic memory (not shown) for storing data.

In operation, the gantry motor control 56 brings the gantry 20 up to rotational speed and the table motor control begins translation of the table 46. The x-ray control 54 turns on the x-ray source 10 and projection data are acquired on a continuous basis. At each beam angle β, the projection acquired comprises of intensity signals identified to each detector element 18' at each particular column and row of the detector array 44.

Referring now to FIGS. 3(a)–(d), a narrow intensity profile 28''' is obtained by breaking of the detector array 44 into columns of multiple detector elements 18' and is significantly narrower than that obtained with a single column CT detector, the latter having a intensity profile equal to the entire detector width of the CT system.

Figure 3A:
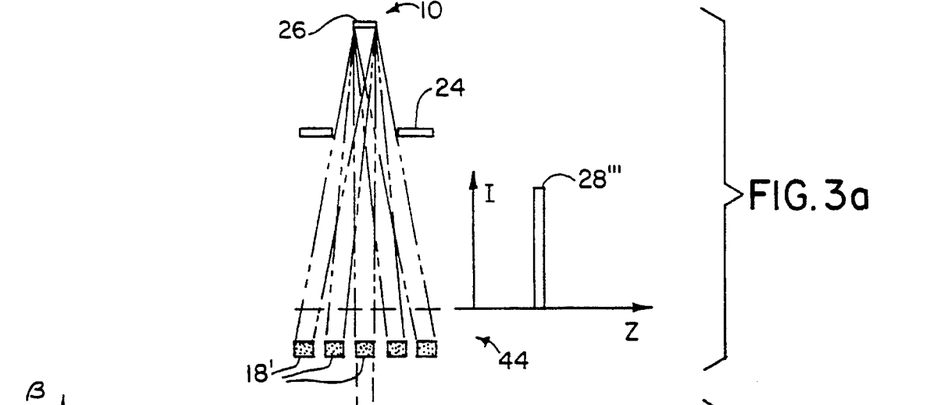
FIG. 3(a) is a cross-section of the entire fan beam and detector array of FIG. 1.
Figure 3B:
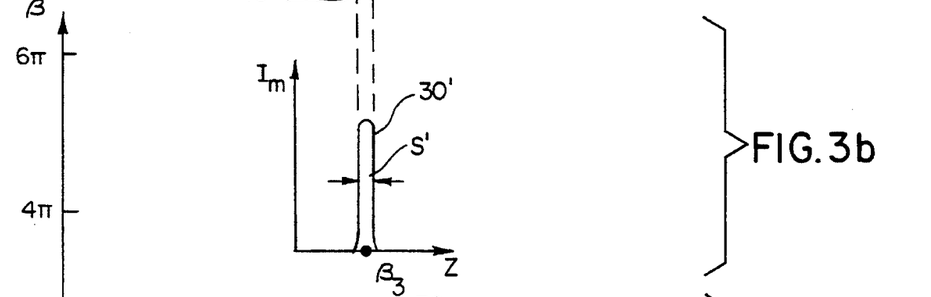
FIG. 3(b) is a graphical representation of the slice profile produced by the fan beam of FIG. 3(a) and a single detector element.
Figure 3C:
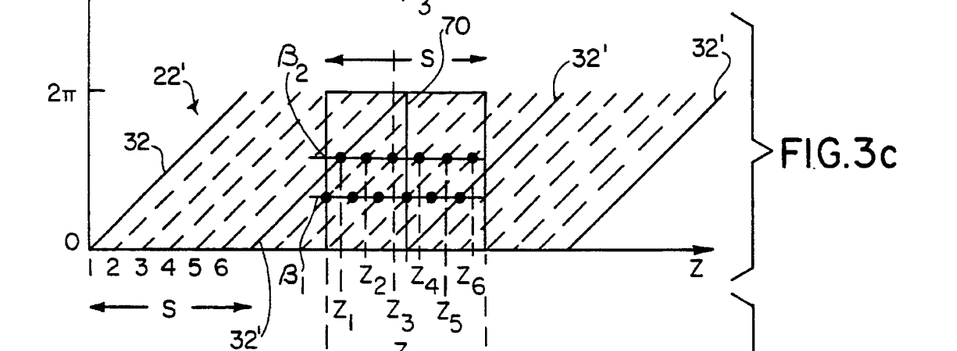
FIG. 3(c) is a graphical representation of the trajectory of each ray associated with a single detector element of FIG. 3(a), with helical scanning, along the z-dimension with increasing beam angle β.

Referring now to FIGS. 1 and 3(c), the CT system of the present invention may employ the same helical pitch of s employed by fan beam CT systems, that is, for each full revolution of the gantry 20, the patient 42 is translated by an amount equal to a slice thickness s as shown by trajectory 32', however, it will be recognized that translation amounts different than s may also be used. In any case, at each beam angle $\beta$ of the gantry 20 multiple intensity signals are obtained along the z-axis from each detector element 18' within a row of the detector array 44. Thus, whereas in a conventional CT system at each beam angle $\beta$, a projection is acquired associated with a single point along the z-axis; in the present invention multiple thin projections are acquired associated with multiple contiguous points along the z-axis.

Each detector element 18' within a row of the detector array 44 may therefore trace its own helix 22' having a pitch s essentially identical to the pitch of a conventional CT machine but interleaved with the helices 22' of the other detector elements 18' within that row. Thus, the spacing along the z-axis between the points at which projection data are acquired by adjacent detector elements 18' within a row is substantially less than s, i.e., less than the spacing along the z-axis between the points at which projection data is acquired by detector elements 18' in consecutive scans of a conventional CT system.

Accordingly, the helically acquired projection set may be interpolated to produce a projection set for an arbitrary slice at position $Z_r$ with two points separated by as little as s' rather than s. As a result, the expansion of the effective beam profile caused by the interpolation to a slice plane at $Z_r$ is much reduced.

Although, in principle, only two points at z-axis positions straddling the slice plane $Z_r$ are required to interpolate an intensity value at the slice plane $Z_r$, in the preferred embodiment, for reasons of providing adequate signal-to-noise ratio, multiple points are used to generate a composite signal and interpolation, as such, is not used.

The intensity signals used for the reconstruction are those from detector elements clustered around the slice plane $Z_r$ for a given projection at a beam angle $\beta$ and at other beam angles $\beta$ preceding or following the given beam angle. For a detector array 44 having six columns and hence six detector elements 18' in each row, for example, six intensity signals which are selected from those projections clustered symmetrically on each side of the desired slice plane $Z_r$.

Referring to FIG. 3(c), at slice plane position $Z_r$, the reconstruction of the slice image requires data for approximately $2\pi$ of gantry rotation represented by projection line 70. For example, the intensity signals for a slice plane image at $Z_r$ for a given angle $\beta_1$ may be generally taken from the first, second, third, fourth, fifth and sixth detector elements 18' corresponding to z-axis locations $Z_1$, $Z_2$, $Z_3$, $Z_4$, $Z_5$, and $Z_6$, all within a row of detector array 44 at one beam angle. For another angle $\beta_2$, however, the helical movement of the gantry means that the z-axis locations of the detector elements 18' within the physical detector array 44, are no longer symmetrically clustered about the z-axis position of the slice plane $Z_r$. Accordingly, the interpolated projection set may employ detector signals from the second, third, fourth, fifth and sixth detector elements 18' of a given row at the beam angle $\beta_2$ and the detector signal from the first detector element of the same row at gantry position $\beta_2+2\pi$.

The operation of the selection of intensity signals during helical scanning results in the intensity signals from detector elements, at one end of the detector array 44, being dropped in favor of the intensity signals from detector elements with successive beam angles $\beta+2\pi$. The intent is to have the multiple z-axis positions of the intensity signals from the detector elements 18' to be close to the position of the slice plane $Z_r$.

Figure 3D:
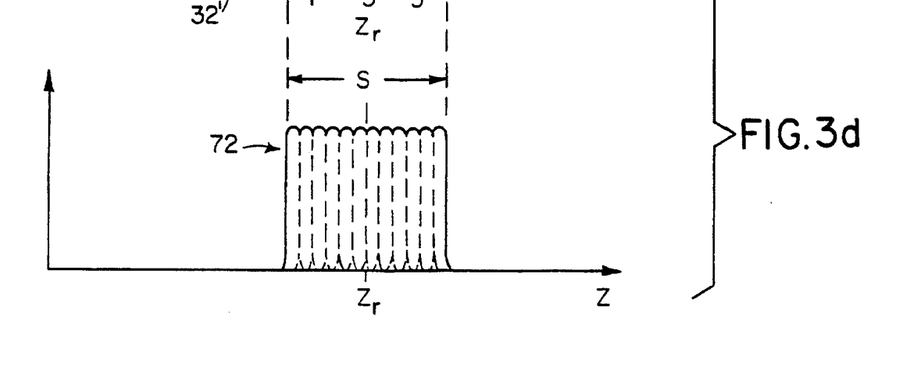
FIG. 3(d) is a graphical representation similar to FIG. 3(b) showing the effective slice profile of the fan beam of FIG. 3(a) after combining a number of single detector elements showing the improved slice profile obtained by the present invention.

When the projection data from corresponding rows of each of the multiple columns (possibly at different beam angles) are added together, the adding has the effect of broadening the effective slice profile s' of an individual detector element 18' to a composite slice profile 72 shown in FIG. 3(d). This composite slice profile 72 has a width approximately equal to s and thus comports with the desired spatial resolution of the CT system and represents a clear advance over the slice profile provided by conventional CT helical scanning with interpolation.

Figure 4A:
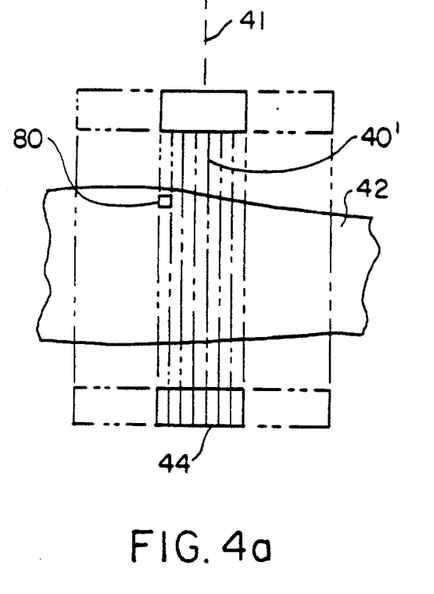
FIGS. 4(a) and 4(b) are exaggerated cross-sections of parallel and diverging fan beams showing the occurrence of multiply-measured volumes of scanning for the diverging fan beam.
Figure 4B:
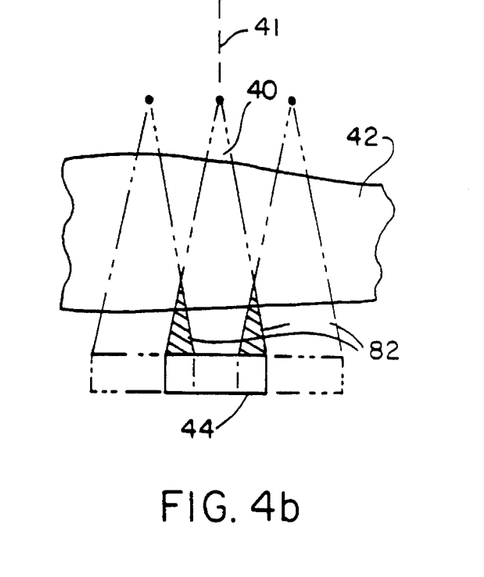

Referring to FIGS. 4(a) and 4(b), the divergence of the fan beam 40 about the gantry plane 38 necessarily provides that some volume elements of the patient will be measured more than once every $2\pi$ of beam angle. In a parallel ray case shown in FIG. 4(a), for every $2\pi$ of beam angle, the detector array 44 may be advanced by its z-axis width to acquire projection data over a contiguous volume of the patient 42, i.e. so that each voxel 80 of the patient 42 is illuminated by one, and no more than one ray, at each $2\pi$ of beam angle $\beta$. In contrast and as shown in FIG. 4(b), the divergence of the fan beam 40 along the z-axis causes it to cover less volume near the focal spot 26 than near the detector array 44. In order to obtain a complete projection set, that is, in order to have each voxel 80 illuminated by at least one ray for each $2\pi$ of beam angle $\beta$, the detector array 44 cannot be advanced by its full z-axis width but must be advanced a lesser amount depending on the exact divergence of the fan beam 40 from the gantry plane 38. This limitation on the amount of translation per beam angle caused by the relative constriction of the fan beam near the source, creates some volumes 82 away from the source which have multiply-measured data, i.e., voxels 80 for which projection data has been acquired for two rays at a beam angles separated by $2\pi$. This multiply-measured data must be accounted for so as to not create artifacts in the reconstructed image. Nevertheless, this multiply measured data may also be used to eliminate artifacts incident to projection domain combination of the projection data per the present invention.

Figure 5:
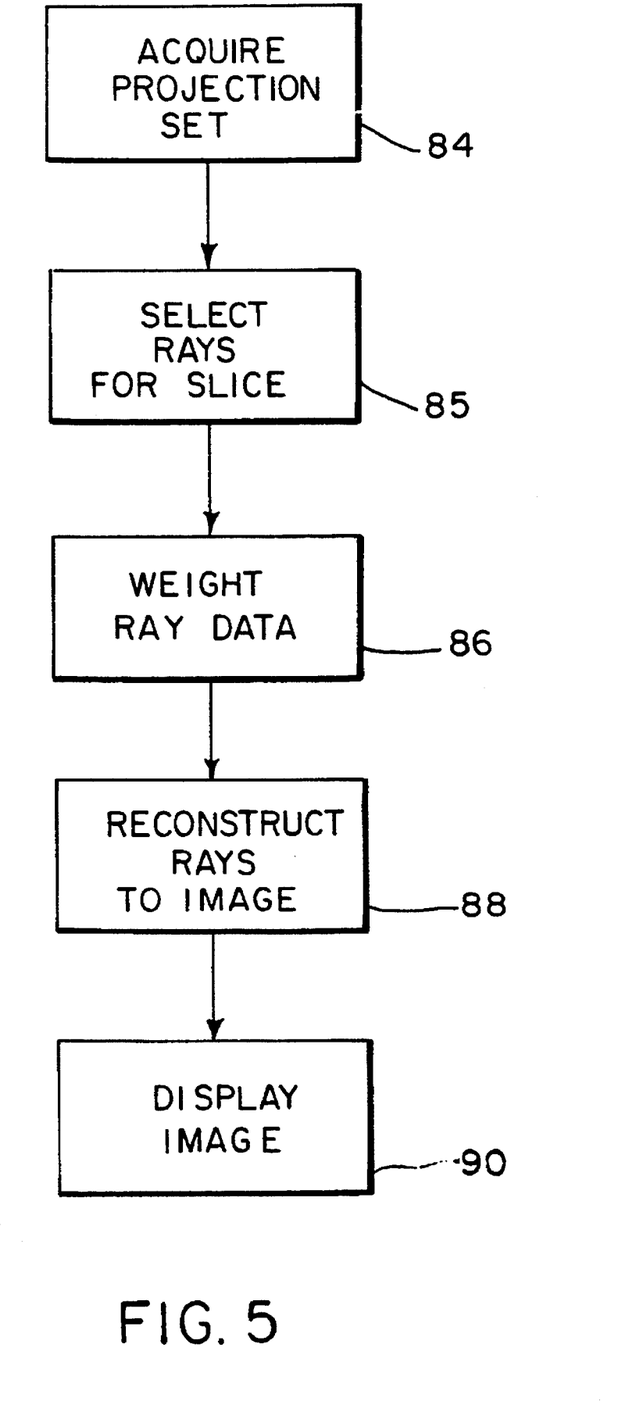
FIG. 5 is a flow chart illustrating the steps of reconstructing the data of the projections in the system of FIG. 1 according to the present invention.

Referring to process block 84 of FIG. 5, the reconstruction process of the present invention begins with the acquisition of projection data over a range of $2\pi$ of beam angle plus $2\gamma_{max}$. Each projection may be identified by its beam angle $\beta$ and by the ray angle $\theta$ and fan beam angle $\gamma$.

A slice to be reconstructed is next identified and projection data for $\pi$ plus $\gamma$ beam angles on either side of the beam angle $\beta_0=\pi$ whose beam axis 41 bisects the slice are collected. Of each conical projection, data from columns receiving rays $\theta$ intersecting the slice 22 are selected as indicated by process block 85. Next according to equation (1) described below, this projection data is weighted according to the beam angle $\beta$ at which it was acquired and data that has a weight less than 1 is combined with corresponding data from beam angles displaced by more than $\pi$ or less than $-\pi$ from the beam angle of the given projection.

Figure 6:
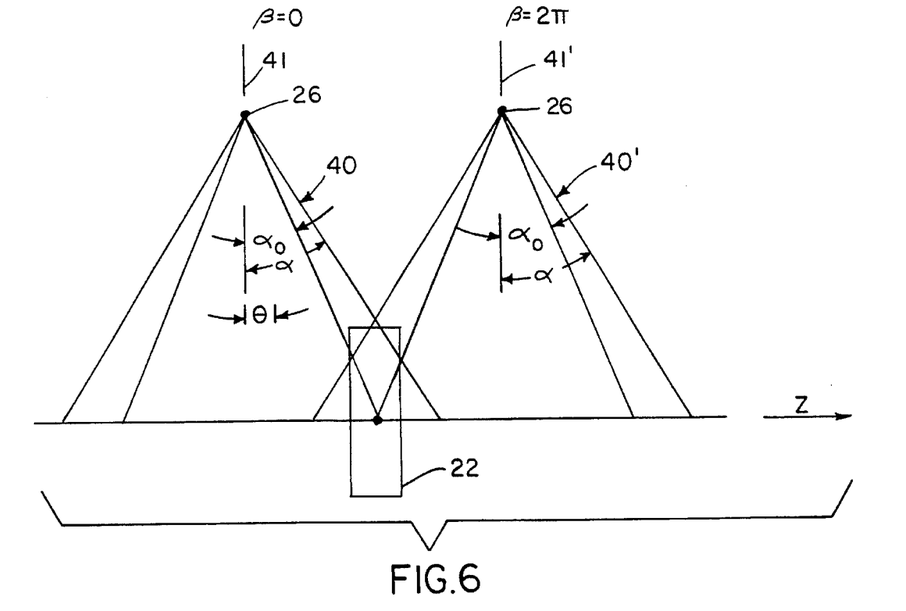
FIG. 6 is an elevational view of two overlapping cone beams in a helical scan displaced by a beam angles of 2π.

Referring now to FIG. 6, the first and last projections for a slice 22 are obtained by two fan beams 40 and 40' at beam angles β=0 and β=2π, where slice 22 is positioned midway between beam axis 41 for the beam 40 at beam angle β=0 and beam axis 41' for the beam 40' at beam angle β=2π. As discussed with respect to FIGS. 4(a) and 4(b), fan beams 40 and 40' overlap to divide the rays of each fan beam 40 and 40' into inner, non-overlapping rays of ray angle θ less than $\alpha_0$ and outer, overlapping rays of ray angle θ greater than $\alpha_0$ and less than α.

Figure 7:
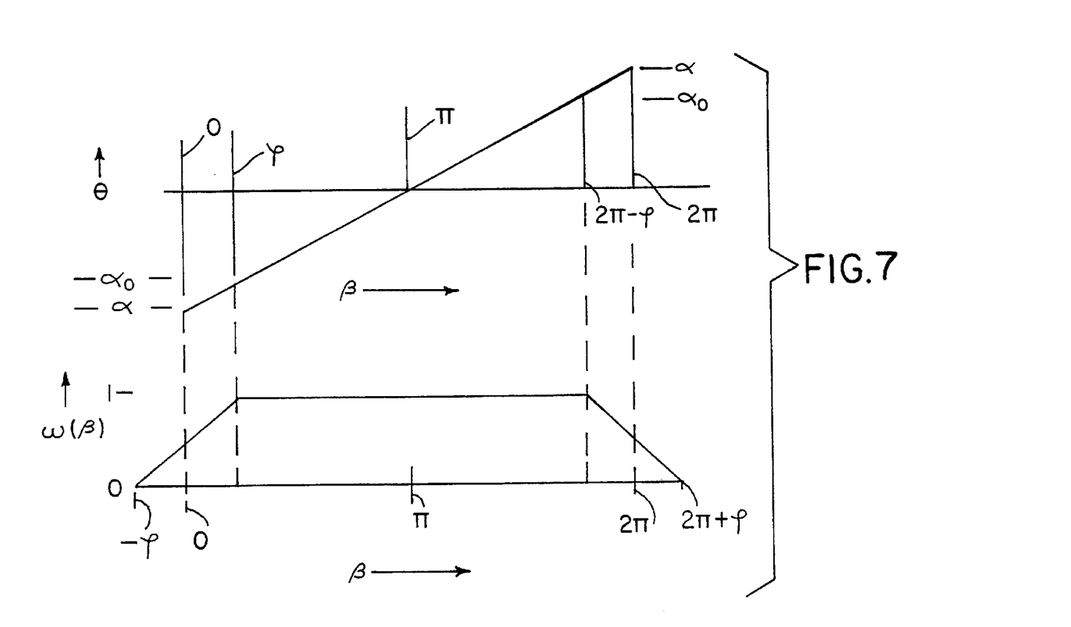
FIG. 7 is a plot of the ray angle of a ray passing through the center of a slice as a function of beam angle β for a range of beam angles used in interpolating to a slice plane, aligned above a plot of weighting factor given to the data from each projection at different angles β.

Referring to FIG. 7, the ray angles θ of those rays passing through slice 22 (selected for reconstructing slice 22 at process block 85 of FIG. 5) becomes progressively greater for projections removed from the beam angle β=π where the fan beam is centered on the slice 22. Specifically, the ray angle θ for the desired rays increases linearly in either direction from β=π to values of α in one direction and decreases linearly to values of −α in the other direction. The rays from each fan beam forming the projection set thus have a marked discontinuity in ray angle θ between the first and last projection of fan beams 40 and 40'. This discontinuity may produce image artifacts.

The present invention recognizes that the discontinuity in ray angle θ may be minimized by making use of the redundant rays of ray angle θ greater than $\alpha_0$ and less than α. In particular, rays taken from a projection β=$β_i$ near the beginning of the projection set (β=0) where rays have ray angles θ of greater than $\alpha_0$ are de-weighted by a function w($β_i$) and summed with rays taken from the next succeeding projection $β_i$+2π which is given the opposite weighting of 1−w($β_i$). That is, the data at the end of the projection set where the relevant rays are highly oblique rays are weighted and combined with data taken at the opposite end of the next projection set so as to minimize the effect of the obliquity. In particular, the projection set may be assembled over 2π of angle β as follows:

$$P'(\beta,\theta) = \begin{cases} w(\beta)P(\beta,\theta) + (1-w(\beta))P(\beta+2\pi,\theta) & \text{when: } 0 \leq \beta < \phi \\ P(\beta,\theta) & \text{when: } \phi \leq \beta < 2\pi - \phi \\ w(2\pi-\beta)P(\beta,\theta) + (1-w(2\pi-\beta))P(\beta+2\pi,\theta) & \text{when: } 2\pi-\phi \leq \beta < 2\pi \end{cases} \quad (1)$$

where:

$$\phi = \pi(\tan\alpha - \tan\alpha_0)/\tan\alpha_0 \quad (2)$$

Referring to FIG. 7, the weighting function w(β) may be a simple linear function such as $$w(\beta) = 0.5(1+\beta/\phi) \quad (3)$$

Referring now to FIG. 5, this weighting, represented by process block 86 may be performed on the raw projection data and thus can be extremely fast.

As indicated by process block 88, the selected and weighted data, combined as necessary, is then reconstructed according to conventional fan beam reconstruction algorithms as are well known in the art. At process block 90, the image of the reconstructed beams is displayed.

Each pair of columns of the detector array may thus produce a single slice image. Alternatively, and as described above with respect to FIGS. 3(a) through 3(b), multiple columns of detector data may be combined to yield a single slice image with an improved z axis profile. In this case after the weighting and combination step of process block 86, multiple intensity signals within a given row of a detector for a given beam angle or beam angles differing by integer multiples of 2π may be combined to build up the necessary aperture width.

While this invention has been described with reference to particular embodiments and examples, other modifications and variations will occur to those skilled in the art in view of the above teachings. Accordingly, the present invention is not limited to the preferred embodiment described herein, but is instead defined in the following claims.

We claim:

1. A computed tomography apparatus producing images of an imaged object having voxels, the apparatus comprising:

an x-ray source directing a beam of x-rays along a beam axis with rotation of the beam axis throughout a plurality of beam angles about a translation axis, the beam including a plurality of rays along paths diverging across the translation axis about a central cone axis at ray angles;

an array of detector elements each receiving a ray after it passes through the imaged object, the elements each producing an intensity signal dependant on the attenuation of the ray associated with that element;

a translator for moving the imaged object along the translation axis with respect to the x-ray source through a plurality of translation positions during the rotation of the beam axis through the plurality of beam angles so that some voxels of the imaged object are illuminated by a first ray at a first beam angle and a second ray at a second beam angle, the first ray and the second ray being associated with beam angles differing by an integer multiple of 2π radians;

a weighting means for weighting the intensity signals associated with the first and second ray prior to reconstruction of a tomographic image to produce weighted intensity signals;

a reconstructor receiving the weighted intensity signals and reconstructing a tomographic image from the weighted intensity signals; and a display for displaying the tomographic image.

2. The apparatus of claim 1, wherein the weighting means weights the first and second intensity signals by weighting values that are a function of the ray angle.

3. The apparatus of claim 1, wherein the weighting means weights the first and second intensity signals by weighting values $w_1$ and $w_2$ where $w_1+w_2=1$.

4. The apparatus of claim 1, wherein beam axes associated with the first and second rays are separated by 2π radians.

5. A method of generating images of an imaged object comprising the steps of:

generating an x-ray beam along a beam axis, the beam including a plurality of rays along paths diverging across a translation axis about a central cone axis at ray angles;

rotating the beam axis throughout a plurality of beam angles about the translation axis;

receiving the rays of the x-ray beam after they pass through the imaged object to produce an intensity signal associated with each ray;

translating the imaged object along the translation axis with respect to the x-ray source during the rotation of the beam axis throughout the plurality of beam angles to obtain a projection set so that at least one voxel of the imaged object is illuminated by a first ray at a first beam angle and a second ray at a second beam angle, the first ray and the second ray being associated with beam angles differing by an integer multiple of $2\pi$ radians;

weighting the intensity signals associated with the first and second ray prior to reconstruction;

reconstructing a tomographic image from the weighted intensity signals from the first and second rays; and displaying an image of the tomographic image.

6. The method of claim 5, wherein the step of weighting weights the first and second intensity signals by weighting values that are a function of the ray angle.

7. The method of claim 5, wherein the weighting means weights the first and second intensity signals by weighting values $w_1$ and $w_2$ where $w_1+w_2=1$.

8. The method of claim 7, wherein the step of translating separates the beam axes associated with the first and second rays by $2\pi$ radians.

* * * * *